United States Patent [19]

Pellico

[11] Patent Number: 5,073,363

[45] Date of Patent: Dec. 17, 1991

[54] FOAMABLE FLUORIDE GELS AND METHOD

[76] Inventor: Michael A. Pellico, 3024 Military Ave., Los Angeles, Calif. 90272

[21] Appl. No.: 465,374

[22] Filed: Jan. 16, 1990

Related U.S. Application Data

[63] Continuation-in-part of Ser. No. 418,251, Oct. 6, 1989.

[51] Int. Cl.$^5$ ............................ A61K 7/16; A61K 7/18
[52] U.S. Cl. ......................................... 424/49; 424/52
[58] Field of Search ............................. 424/45, 49, 52; 433/215, 217.1; 106/35

[56] References Cited

U.S. PATENT DOCUMENTS

| | | | |
|---|---|---|---|
| 4,137,303 | 1/1979 | Gaffar et al. | 424/52 |
| 4,601,898 | 7/1986 | Stier et al. | 424/52 |
| 4,770,634 | 9/1988 | Pellico | 433/217.1 |

*Primary Examiner*—Nathan M. Nutter
*Attorney, Agent, or Firm*—Donald Diamond

[57] ABSTRACT

An acidified and foamable fluoride gel composition, for use in dental therapy, is provided that contains water, dental fluoride, foaming agent, gelling agent and acidifying agent. An illustrative composition comprises water, sodium fluoride, Pluronic F108 nonionic surfactant and phosphoric acid. The foamable fluoride gel composition, which is packaged in a suitable container, is dispensed onto a toothbrush, or the like, for application to the teeth to be treated to thereby effect fluoride uptake by the dental enamel. The foamable fluoride gel provides substantially the same fluoride uptake as a tray fluoride gel but this result is achieved by a foamable fluoride gel with substantially less fluoride than that which is present in a tray fluoride.

20 Claims, No Drawings

FOAMABLE FLUORIDE GELS AND METHOD

CROSS-REFERENCE TO RELATED APPLICATION

This application is a continuation-in-part of U.S. patent application Ser. No. 418,251, filed Oct. 6, 1989 and entitled Foamable Fluoride Compositions and Method.

BACKGROUND OF THE INVENTION

This invention relates to dental compositions and, more particularly, to acidified fluoride gels which are adapted to foam upon oral application by brushing or the like.

It is generally understood in the dental art that certain kinds of food actuated decay are initiated by acid etching of the tooth enamel with the source of the acid being a metabolite resulting from bacterial and enzymatic action on food particles in the oral cavity. It is generally accepted that plaque—which is a soft accumulation on the tooth surfaces consisting of an organized structure of micro-organisms, proteinaceous and carbohydrate substances, epithelial cells, and food debris—is a contributory factor in the development of various pathological conditions of the teeth and soft tissue of the oral cavity. It has been suggested that the saccharolytic organisms of the oral cavity, which are associated with the plaque, cause decalcification beneath the plaque matrix through metabolic activity which results in the accumulation and localized concentration of organic acids. The etching and decalcification of the enamel may continue until the pulp chamber of the tooth is reached.

Fluoride compounds have been incorporated into dental topicals and into consumables to provide an orally beneficial effect by reducing the dissolving action of acids on dental enamel. It has been reported that the fluoride combines with hydroxyapatite, the crystalline structure of the teeth, to produce a modified crystalline structure which is more resistant to acid attack.

Diverse fluoride compounds have been disclosed in the prior art for use in dental care including, for example, sodium fluoride, sodium monofluorophosphate, stannous fluoride, fluoroalkyl phosphates, and quaternary ammonium fluorides.

The fluorides can be incorporated into gels, rinses, toothpaste, tooth powder, chewing gum and the like for topical application. Fluoride treatment can also be undertaken through consumables such as fluoridated drinking water and fluoride tablets.

U.S. Pat. No. 4,137,303 (Gaffar, et al., 1979) discloses an antibacterial antiplaque mouthwash which may also contain a surface active agent and/or a fluoride-providing compound. The patentees, in an illustrative embodiment, disclose a mouthwash formulation containing flavored alcohol, Pluronic F-108, glycerine, benzethonium chloride, sodium saacharin, a polyamine polyphosphonic compound and water, with the pH adjusted to 8.0.

Caslavska, V.: Effect of Surface-Active Agents on Fluoride-Enamel Interactions, Caries Res. 17: 221-228 (1983), discloses an in vitro study wherein blocks of human enamel were treated with aqueous solutions containing fluoride in combination with surface-active agents and it was reported that surface-active agents may affect fluoride penetration into the enamel in a negative or positive way and further they they may affect fluoroapatite formation.

U.S. Pat. No. 4,601,898 (Stier, et al., 1986) discloses an anti-caries mouthrinse containing titanium tetrafluoride stabilized with a chelating agent such as citric acid and which can be further formulated with alcohol, a humectant such as glycerin or aqueous sorbitol, and sufactants including cationic, anionic and nonionic surfactants. The patentees, in an illustrative embodiment, disclose a mouthrinse formulation containing titanium tetrafluoride, sodium citrate, Pluronic F-127, flavor, dye, sodium saacharin and water.

U.S. Pat. No. 4,770,634 (Pellico, 1988) discloses a foamable fluoride composition for use in dental therapy. An illustrative composition contains water, sodium fluoride, sucrose disterate, glycerol and phosphoric acid. The foamable fluoride composition, which is packaged in an aerosol container in combination with an aerosol propellant, is dispensed into the trough of a dental tray as a dense, stable, non-flowable foam which is superimposed about and into engagement with the teeth to be treated to thereby effect fluoride uptake by the dental enamel.

Heretofore, fluoride gels have been used in professional dental practice to topically apply fluoride to the teeth. The fluoride gel is usually supplied as a thick gel in a plastic bottle from which it is dispensed into the trough of a plastic dental tray that is inserted into the mouth in juxtaposition to the teeth whereby the teeth engage the gel for about 1 to 4 minutes, as per the supplier's instructions.

A typical fluoride gel contains water, a water soluble dental fluoride such as sodium fluoride, glycerol, an acidifying agent such as phosphoric acid, and a water soluble thickener such as carboxmethyl cellulose, polyvinyl alcohol, or xanthan gum.

An illustrative fluoride gel formulation is as follows:

| INGREDIENTS | PARTS BY WEIGHT |
| --- | --- |
| Water | 85.5 |
| Sodium fluoride | 2.7* |
| Xanthan gum | 3.2 |
| Glycerol | 3.4 |
| Phosphoric acid (85%) | 4.1 |

*Available fluoride 1.2 pts. by wt.

The water soluble thickener is selected so as to provide a highly viscous and thick system for maintaining the gel in the tray and in positive contact with the teeth, since a thin gel would tend to flow away from the tooth surface and thereby reduce fluoride uptake by the tooth and, additionally, a thin gel could flow out of the tray and cause the patient to gag and choke.

The acidifying agent is selected so as to provide the fluoride gel with a pH between about 3.0 and 4.5 which facilitates and enhances fluoride uptake by the teeth.

There are several problems associated with the use of fluoride gels in dental therapy. One of the most vexing problems is that of viscosity. The fluoride gel must be thick enough so that it does not flow out of the dental tray while the tray is in the patient's mouth and, at the same time, the gel must be thin enough to be dispensed from a plastic bottle into the tray in preparation for the fluoride treatment. Because it is extremely difficult to formulate a fluoride gel that flows from a plastic dispensing bottle and yet remains stationary in the dental tray for up to 4 minutes while in the mouth, the fluoride gels heretofore available had a tendency to flow while in the tray and cause patient gagging during the course of treatment.

Another problem associated with fluoride gels is that of toxicity. Fluorides have a low concentration threshold for exerting toxic effects. It is reported that severe symptons can be manifested from the ingestion of less than one gram of sodium fluoride. Thus, the ingestion of any significant amount of fluoride gel can produce serious consequences. This risk is especially noteworthy because fluoride gels, which have been flavored to mask the acidic taste, are most often used to treat children and the flavoring can increase the chance of unintentionally swallowing a significant amount of the semi-fluid gel.

A further problem associated with fluoride gels is the cost-effectiveness of the thick gel. In view of the high viscosity of the fluoride gels, the only fluoride which is available for uptake by the tooth is that which is in the immediate vicinity of the tooth surface. The remaining fluoride, which is the bulk of the fluoride in the tray, is unavailable for dental uptake because fluoride movement is restricted by the high viscosity of the gel.

Accordingly, it would be advantageous to provide an acidified and foamable fluoride gel for use in professional dental therapeutics that can be dispensed from a tube and applied with a brush or other suitable applicator and which requires less gel and, therefore, less fluoride to achieve substantially the same fluoride uptake as that obtained with a conventional tray fluoride in gel form.

SUMMARY OF THE INVENTION

In accordance with one aspect of this invention, there is provided an acidified and foamable fluoride gel composition comprising:

(a) an acid stable and orally compatible, water miscible, gelling agent in an amount to impart stable gel characteristics to the gel composition;

(b) an acid stable and orally compatible, water miscible, foaming agent in an amount to provide a stable foam upon oral application of the gel composition;

(c) an orally compatible acidifying agent in an amount to provide the gel composition with a pH between about 3.0 and about 4.5;

(d) a water soluble dental fluoride in an amount to provide the gel composition with about 0.5 to about 5.0 wt.% available fluoride; and (e) water to 100 wt.%.

In accordance with a second aspect of this invention, there is provided a method for treating teeth with a fluoride composition which comprises applying to the teeth to be treated an acidified and foamable fluoride composition containing: (a) an acid stable and orally compatible, water miscible, gelling agent in an amount to impart stable gel characteristics to the gel composition; (b) an acid stable and orally compatible, water miscible, foaming agent in an amount to provide a stable foam upon oral application of the gel composition; (c) an orally compatible acidifying agent in an amount to provide the gel composition with a pH between about 3.0 and about 4.5; (d) a water soluble dental fluoride in an amount to provide the gel composition with about 0.5 to about 5.0 wt.% available fluoride; and (e) water to 100 wt.%.

DETAILED DESCRIPTION

The acidified and foamable fluoride gels of this invention comprise water, water soluble dental fluoride, foaming agent, gelling agent and acidifying agent.

Water soluble dental fluorides which can be used in the practice of this invention are those which are approved by governmental agencies for oral care. The dental fluoride is generally present in the fluoride gel composition in an amount to provide the composition with about 0.5 to about 5.0 wt.% available fluoride and preferably in an amount to provide the composition with about 1.0 to about 2.5 wt.% available fluoride. Sodium fluoride is particularly well suited for use in fluoride therapy and, when so used, is generally present in the acidified and foamable fluoride gel composition in an amount from about 1.1 to about 11.1 wt.% and, preferably, in an amount from about 2.2 to about 5.6 wt.%.

Foaming agents which can be used in the practice of this invention to produce stable foams upon oral application of the acidified fluoride gel composition include nonionic surfactants, anionic surfactants, cationic surfactants, and amphoteric surfactants as well as mixtures thereof.

Illustrative nonionic foaming surfactants include: (a) ethoxylated polyoxypropylene adduct of propylene glycol available under the trademark Pluronic from BASF Corporation, Parsippamy, N.J. 07054; (b) ethoxylated alkyl phenol available under the trademark IGEPAL from GAF Corporation, Wayne, N.J. 07470 and under the trademark Tergitol from Union Carbide Corporation, Danbury, Conn. 06817; (c) amine oxide available under the trademark Incromine from Croda Surfactants, New York, N.Y. 10016; and (d) sucrose fatty acid ester available under the trademark Crodesta SL-40.

The nonionic surfactants which are used in the practice of this invention should be so selected as to provide suitable foaming characteristics upon oral application of the composition and, with respect to this feature, should have an HLB value of at least about 12.

The Pluronic surfactants which can be used in this invention comprise block copolymers of polyoxyethylene and polyoxypropylene having an average molecular weight from about 3,000 to about 15,000, with an intermediate average molecular weight being from about 6,000 to about 15,000 and a preferred average molecular weight being from about 10,000 to about 15,000. The ethoxylated portion of the block copolymer generally constitutes from about 30 to about 80% by weight of the molecule, with an intermediate range being from about 40 to 80%, by weight, of the molecule and a preferred percentage being from about 70 to about 80%, by weight, of the molecule. Good results are achieved with (a) Pluronic F108 which has an average molecular weight of 14,600, a polyoxyethylene content of about 80 wt.%, and an HLB value in excess of 24, and with (b) Pluronic F127 which has an average molecular weight of 12,600, a polyoxyethylene content of about 70 wt.%, and an HLB value from 18 to 23.

The orally compatible and acid stable foaming agent is generally present in the fluoride gel composition in an amount from about 0.4 to about 20.0 wt.% and, preferably, in an amount from about 1.0 to about 11.0 wt.%.

Gelling agents which can be used in the practice of this invention include natural gums, synthetic gums and mixtures thereof, which are orally compatible, water miscble and acid stable. A suitable gelling agent, which has the requisite characteristics for use in the compositions of this invention is xanthan gum. The gelling agent is generally present in the fluoride gel composition in an amount from about 0.5 to about 10.0 wt.% and, preferably in an amount from about 1.5 to about 5.0 wt.%.

Acidifying agents which can be used in the practice of this invention to facilitate and enhance fluoride uptake by the tooth structure from the fluoride gel are those which are orally compatible and include, for example, phosphoric acid. The acidifying agent is generally present in the fluoride gel composition in an amount to provide the gel with a pH from about 3.0 to about 4.5.

As an adjunct to the water soluble fluoride and the acidifying agent, the fluoride gel compositions may advantageously contain hydrofluoric acid in an amount from about 0.20 to about 0.80 wt.% and, preferably, in an amount from about 0.35 to about 0.65 wt.%.

Glycerol, a sweetener can be included in the fluoride gel composition to improve flavor and, when so used, is generally present in an amount up to about 22 wt.%.

The fluoride gel compositions are prepared by blending dental fluoride, foaming agent, gelling agent and acidifying agent with water under moderate mixing conditions at ambient temperature. To enhance product integrity, the phosphoric acid acidifying agent is preferably added to the ingredient mix as substantially the last ingredient. The resulting fluoride gel composition is suitably packaged for dispensing onto a toothbrush or other type applicator for applying the composition to the teeth. The foamable gel composition is maintained in engagement with the teeth for a sufficient length of time to effect fluoride uptake by the teeth, usually for about 1 to 4 minutes, and then is rinsed from the teeth and discharged from the mouth.

EXAMPLE I

The following examples illustrate various ingredients and concentrations which can be used in the preparation of the acidified and foamable fluoride gel compositions of this invention.

1(a)

| INGREDIENTS | PARTS BY WEIGHT |
| --- | --- |
| Water | 69.3 |
| Sodium Fluoride* | 2.4 |
| Pluronic F108** | 1.0 |
| Xanthan Gum | 2.0 |
| Hydrofluoric Acid | 0.5 |
| Glycerol | 21.3 |
| Sodium Saccharin | 0.1 |
| Phosphoric Acid (85%) | 3.0 |
| Flavor and Color | 0.4 |

*Available fluoride 1.1 pts. by wt.
**Pluronic F108 is the trademark for an ethoxylated polyoxypropylene adduct of propylene glycol having an average molecular weight of 14,600, a polyoxyethylene content of 80 wt. %, and an HLB value in excess of 24.

1(b)

| INGREDIENTS | PARTS BY WEIGHT |
| --- | --- |
| Water | 68.8 |
| Sodium Fluoride | 2.4 |
| Pluronic F127* | 10.0 |
| Xanthan Gum | 1.0 |
| Glycerol | 11.8 |
| Sodium Saccharin | 0.1 |
| Hydrofluoric Acid | 0.5 |
| Phosphoric Acid (85%) | 3.0 |
| Flavor and Color | 0.4 |

*Pluronic F127 is the trademark for an ethoxylated polyoxypropylene adduct of propylene glycol having an average molecular weight of 12,600, a polyoxyethylene content of 70 wt. %, and an HLB value from 18 to 23.

1(c)

| INGREDIENTS | PARTS BY WEIGHT |
| --- | --- |
| Water | 68.8 |
| Sodium Fluoride | 2.4 |
| Igepol CA-630* | 0.5 |
| Xanthan Gum | 2.0 |
| Glycerol | 22.3 |
| Sodium Saccharin | 0.1 |
| Hydrofluoric Acid | 0.5 |
| Phosphoric Acid (85%) | 3.0 |
| Flavor and Color | 0.4 |

*Igepol CA-630 is the trademark for octylphenol condensed with 8 moles of ethylene oxide.

1(d)

| INGREDIENTS | PARTS BY WEIGHT |
| --- | --- |
| Water | 69.3 |
| Sodium Fluoride | 2.4 |
| Tergitol NP-9* | 3.0 |
| Xanthan Gum | 2.0 |
| Glycerol | 19.8 |
| Sodium Saccharin | 0.1 |
| Phosphoric Acid (85%) | 3.0 |
| Flavor and Color | 0.4 |

*Tergitol NP-9 is the trademark for a nonylphenol ethoxylate containing 9 moles of ethylene oxide.

1(e)

| INGREDIENTS | PARTS BY WEIGHT |
| --- | --- |
| Water | 69.3 |
| Sodium Fluoride | 2.4 |
| Igepon T-33* | 1.5 |
| Xanthan Gum | 2.0 |
| Glycerol | 20.8 |
| Sodium Saccharin | 0.1 |
| Phosphoric Acid (85%) | 3.0 |
| Flavor and Color | 0.4 |

*Igepon T-77 is the trademark for sodium N-methyl-N-oleoyltaurate.

1(f)

| INGREDIENTS | PARTS BY WEIGHT |
| --- | --- |
| Water | 69.3 |
| Sodium Fluoride | 2.4 |
| Crodesta SL-40* | 15.0 |
| Xanthan Gum | 2.0 |
| Glycerol | 1.8 |
| Tween 60 | 6.0 |
| Sodium Saccharin | 0.1 |
| Phosphoric Acid (85%) | 3.0 |
| Flavor and Color | 0.4 |

*Crodesta SL-40 is the trademark for a sucrose stearate.

1(g)

| INGREDIENTS | PARTS BY WEIGHT |
| --- | --- |
| Water | 69.3 |
| Sodium Fluoride | 2.4 |
| Incromine Oxide L* | 0.5 |

1(g)

| INGREDIENTS | PARTS BY WEIGHT |
| --- | --- |
| Xanthan Gum | 2.0 |
| Glycerol | 22.3 |
| Sodium Saccharin | 0.1 |
| Phosphoric Acid (85%) | 3.0 |
| Flavor and Color | 0.4 |

*Incromine Oxide L is the trademark for lauryl dimethylamine oxide (lauramine oxide).

1(h)

| INGREDIENTS | PARTS BY WEIGHT |
| --- | --- |
| Water | 69.3 |
| Sodium Fluoride | 2.4 |
| CEM-38* | 2.0 |
| Xanthan Gum | 2.0 |
| Glycerol | 20.3 |
| Sodium Saccharin | 0.1 |
| Phosphoric Acid (85%) | 3.0 |
| Flavor and Color | 0.4 |

*CEM-38 is the trademark for cocoamphocarboxyglycinate.

In view of the foregoing description and examples, it will be come apparent to those of ordinary skill in the art that equivalent modifications thereof may be made without departing from the spirit and scope of this invention.

That Which Is Claimed Is:

1. An acidified and foamable fluoride gel composition comprising:
   an acid stable and orally compatible, water miscible, gelling agent in an amount to impart stable gel characteristics to the gel composition;
   an acid stable and orally compatible, water miscible, foaming agent in an amount to provide a stable foam upon oral application of the gel composition;
   an orally compatible acidifying agent in an amount to provide the gel composition with a pH between about 3.0 and about 4.5;
   a water soluble dental fluoride in an amount to provide the gel composition with about 0.5 to about 5.0 wt.% available fluoride; and
   water to 100 wt.%.

2. The gel composition of claim 1 wherein the gelling agent is a natural gum, a synthetic gum or mixtures thereof.

3. The gel composition of claim 2 wherein the gelling agent is xanthan gum at a concentration from about 0.5 to about 10.0 wt.%.

4. The gel composition of claim 3 wherein the concentration of xanthan gum is from about 1.5 to about 5.0 wt.%.

5. The gel composition of claim 1 wherein the foaming agent is a nonionic surfactant, anionic surfactant, cationic surfactant, amphotertic surfactant, or mixtures thereof.

6. The gel composition of claim 5 wherein the concentration of the foaming agent is from about 0.4 to about 20 wt.%.

7. The gel composition of claim 5 wherein the foaming agent is an ethoxylated polyoxypropylene adduct of propylene glycol having an average molecular weight from about 3,000 to about 15,000 and is present in an amount from about 1.0 to about 11.0 wt.%.

8. The gel composition of claim 6 wherein the foaming agent is an ethoxylated alkylphenol.

9. The gel composition of claim 6 wherein the foaming agent is sodium N-methyl-N-oleoyltaurate.

10. The gel composition of claim 6 wherein the foaming agent is a sucrose ester of a fatty acid.

11. The gel composition of claim 6 wherein the foaming agent is an amine oxide.

12. The gel composition of claim 6 wherein the foaming agent is cocoamphocarboxyglycinate.

13. The gel composition of claim 1 wherein the acidifying agent is phosphoric acid.

14. The gel composition of claim 13 which further includes hydroflouric acid in an amount from about 0.05 to about 0.20 wt.%.

15. The gel composition of claim 1 wherein the dental fluoride is sodium fluoride.

16. A method for treating teeth with a fluoride composition which comprises:
    applying to the teeth to be treated an acidified and foamable fluoride composition containing:
    an acid stable and orally compatible, water miscible, gelling agent in an amount to impart stable gel characteristics to the gel composition;
    an acid stable and orally compatible, water miscible, foaming agent in an amount to provide a stable foam upon oral application of the gel composition;
    an orally compatible acidifying agent in an amount to provide the gel composition with a pH between about 3.0 and about 4.5;
    a water soluble dental fluoride in an amount to provide the gel composition with about 0.5 to about 5.0 wt.% available fluoride; and
    water to 100 wt.%.

17. The method of claim 16 wherein the gelling agent is xanthan gum in an amount from about 0.5 to about 10.0 wt.%.

18. The method of claim 17 wherein the foaming agent is a nonionic surfactant, anionic surfactant, cationic surfactant, amphotertic surfactant, or mixtures thereof in an amount from about 0.4 to about 20 wt.%.

19. The method of claim 18 wherein the acidifying agent is phosphoric acid, the dental fluoride is sodium fluoride and the composition further includes hydrofluoric acid in an amount from about 0.05 to about 0.20 wt.%.

20. The method of claim 19 wherein the foaming agent is an ethoxylated polyoxypropylene adduct of propylene glycol having an average molecular weight from about 3,000 to about 15,000 and is present in an amount from about 1.0 to about 11.0 wt.%.

* * * * *